US007073733B2

(12) United States Patent
Cohen et al.

(10) Patent No.: US 7,073,733 B2
(45) Date of Patent: Jul. 11, 2006

(54) MICRODISPENSING PUMP

(75) Inventors: Ben Z. Cohen, 140 E. 80th St., New York, NY (US) 10021; Nigel Kelly, Rye, NY (US)

(73) Assignee: Ben Z. Cohen, New York, NY (US)

( * ) Notice: Subject to any disclaimer, the term of this patent is extended or adjusted under 35 U.S.C. 154(b) by 149 days.

(21) Appl. No.: 10/490,183

(22) PCT Filed: Sep. 20, 2002

(86) PCT No.: PCT/US02/29892

§ 371 (c)(1),
(2), (4) Date: Jul. 26, 2004

(87) PCT Pub. No.: WO03/024823

PCT Pub. Date: Mar. 27, 2003

(65) Prior Publication Data

US 2004/0262423 A1 Dec. 30, 2004

Related U.S. Application Data

(60) Provisional application No. 60/323,659, filed on Sep. 20, 2001.

(51) Int. Cl.
*A61M 11/02* (2006.01)
*B05B 9/04* (2006.01)

(52) U.S. Cl. .......................... 239/373; 239/88; 239/89

(58) Field of Classification Search .................. 239/88, 239/89, 333, 337, 349, 251, 359, 360, 373, 239/302; 222/321.1, 321.2, 321.7, 321.8, 222/341, 383.1, 385

See application file for complete search history.

(56) References Cited

U.S. PATENT DOCUMENTS

| | | | | |
|---|---|---|---|---|
| 3,771,420 | A | 11/1973 | Buchtel | |
| 4,335,835 | A | 6/1982 | Beigler et al. | |
| 4,479,797 | A | 10/1984 | Kobayashi et al. | |
| 4,848,598 | A | 7/1989 | McKinney | |
| 5,358,149 | A * | 10/1994 | O'Neill | 222/321.2 |
| 5,467,900 | A * | 11/1995 | Maas et al. | 222/341 |
| 5,649,649 | A * | 7/1997 | Marelli | 222/321.2 |
| 5,947,340 | A * | 9/1999 | Arnold et al. | 222/321.9 |
| 6,083,762 | A * | 7/2000 | Papen et al. | 436/180 |
| 6,913,169 | B1 * | 7/2005 | Lee | 222/321.2 |

* cited by examiner

*Primary Examiner*—David A. Scherbel
*Assistant Examiner*—James S. Hogan
(74) *Attorney, Agent, or Firm*—Hoffmann & Baron, LLP

(57) ABSTRACT

Several different features are provided for use with a pump, particularly a microdispensing pump. In a first aspect of the subject invention, latch fingers are provided which coact with a stop member to yieldingly inhibit movement of an actuator of the pump to ensure sufficient momentum is provided to the pump for actuation. In a second aspect of the invention, an overcap is provided which defines an at least liquid-tight seal with the pump body at locations spaced from a nozzle of the pump to limit ingress of contaminants into the nozzle. In a third aspect, at least one protruding bead is provided in proximity to at least one edge of a label mounted to the pump body to restrict removal thereof. In a fourth aspect, at least one rib is provided in proximity to a dispensing cap to provide lateral stability thereto.

17 Claims, 9 Drawing Sheets

MICRODISPENSING PUMP

CROSS-REFERENCE TO RELATED APPLICATION

This application claims priority of U.S. Provisional Application No. 60/323,659, filed Sep. 20, 2001.

BACKGROUND OF THE INVENTION

Microdispensing pumps are known in the prior art, such as those disclosed in U.S. Pat. No. 5,881,956; WIPO PCT Published Application No. WO 01/14245; and related applications. The entire disclosures of these references are incorporated by reference herein.

Although microdispensing pumps are known in the prior art, problems still exist with their operation and storage. For example, with a microdispensing pump used in an ophthalmic application, ingress of dirt into the pump's nozzle is a major concern. With prior art eye dropper bottle designs, a threaded overcap is typically provided which is formed to sufficiently thread onto a dropper bottle body to press against and form a tight mechanical seal against the dispensing aperture of the dropper bottle. However, with a microdispensing pump, such a design is not practicable, because of the nozzle orientation (i.e., being transverse to the longitudinal axis of the pump body), as well as, the simple fact that movement of the nozzle, vis-á-vis the dispensing cap, may result in inadvertent actuation of the pump. With eye dropper bottles, tight contact between an overcap and a dispensing aperture does not result in an inadvertent administration of fluid.

SUMMARY OF THE INVENTION

Various shortcomings associated with the prior art are addressed with the subject invention. Different features of a microdispensing pump are described herein which may be used in various combinations, or each singularly, and also may be used in various pump applications, not limited to microdispensing pumps. Some of the features are particularly well-suited for applications where accurate dosing is desired, such as with ophthalmic applications.

In a variation of the first aspect of the subject invention, a pump is provided including a plurality of cantilevered fingers; a piston is disposed to slidably move at least partially within the fingers; and, a stop member is at least partially disposed about the piston, the stop member and the fingers being fixed to the pump body such that movement of the piston results in relative movement between the fingers and the stop member. In addition, the stop member is located to be contacted by the fingers upon a predetermined extent of relative movement between the stop member and the fingers, with the fingers flexing upon contacting the stop member such that the fingers yieldingly inhibit movement of the piston. Accordingly, a predetermined amount of force is required to overcome the resistance provided by the fingers. In this manner, sufficient momentum must be required to actuate the pump to ensure delivery of a proper dose, as disclosed in U.S. Pat. No. 5,881,956.

In a second aspect of the subject invention, a pump is provided having an overcap formed to removably mount onto a pump body, the overcap defining an at least liquid-tight seal with the pump body at locations spaced from a nozzle on the pump body. In this manner, the overcap can be used to restrict the introduction of dirt, debris and other contaminants to the nozzle of the pump, with the pump not being in use. As such, the pump can be provided with a sufficiently proper seal which can withstand hazardous conditions, including those rigorous conditions imposed by CCIT (container closure integrity testing).

In a third aspect of the subject invention, a pump is provided having at least one bead protruding from a pump body in proximity to at least one edge of a label mounted to the pump body. Particularly with labels having instructions and/or warnings, inadvertent or improper removal of the label is highly undesired. With the subject invention, removal of the label can be restricted.

In a fourth aspect of the subject invention, a pump is provided with a pump body including a dispensing cap with a nozzle, the dispensing cap being movable to actuate the pump. In one variation, at least one channel is formed in the dispensing cap and at least one rib extends into each of the channels of the dispensing cap. The ribs each have a sufficient length to at least extend substantially through the respective channel along full extent of movement of the dispensing cap. With the rib-channel interface, sideward movement of the dispensing cap can be limited. This is particularly desirable where straight-line application of force to the dispensing cap is relied on to actuate the pump.

These and other features of the invention will be better understood through a study of the following detailed description and accompanying drawings.

DETAILED DESCRIPTION OF THE INVENTION

Figure 1:
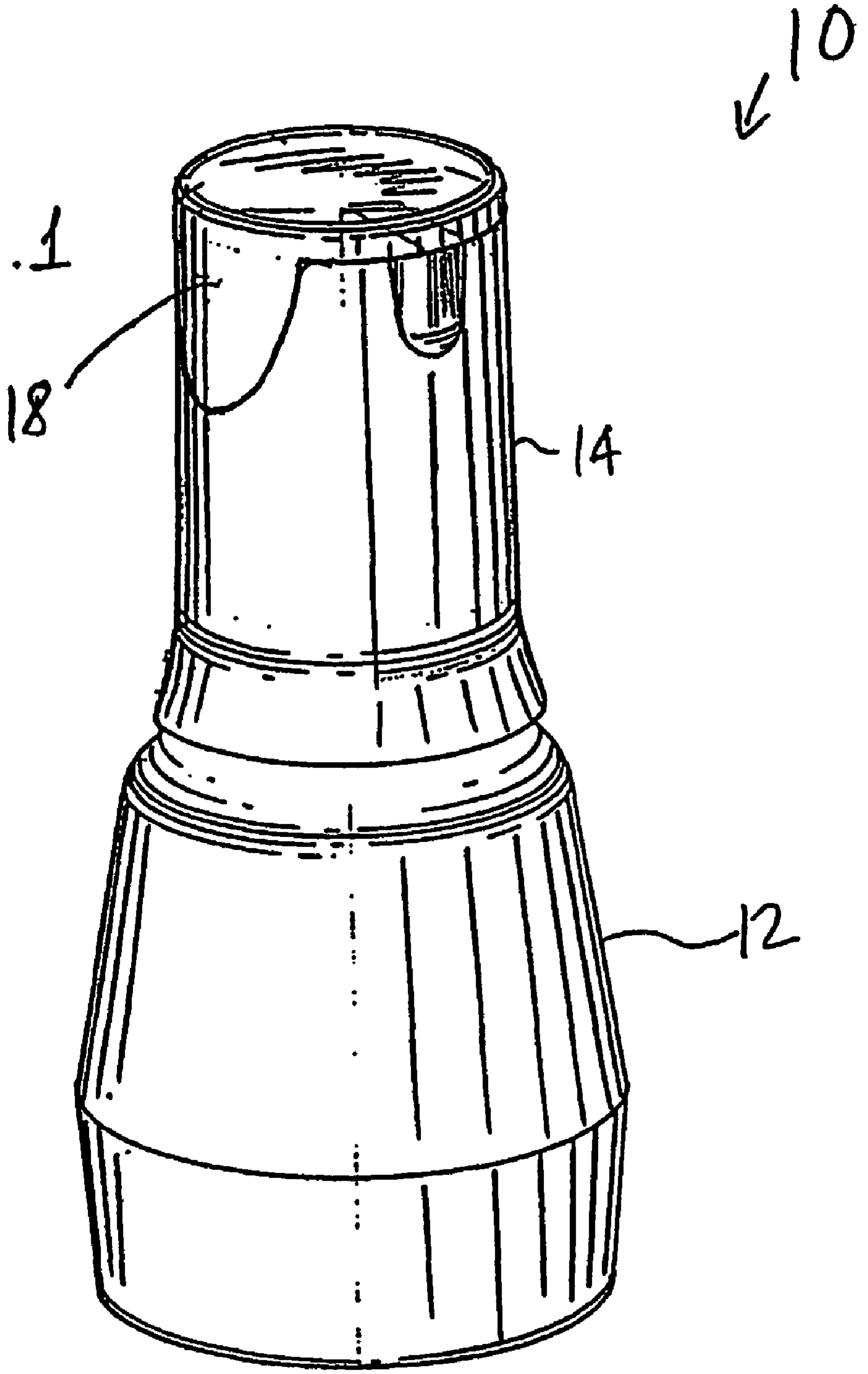
FIGS. 1 and 2 are perspective views of a pump which may use one or more aspects of the subject invention.
Figure 2:
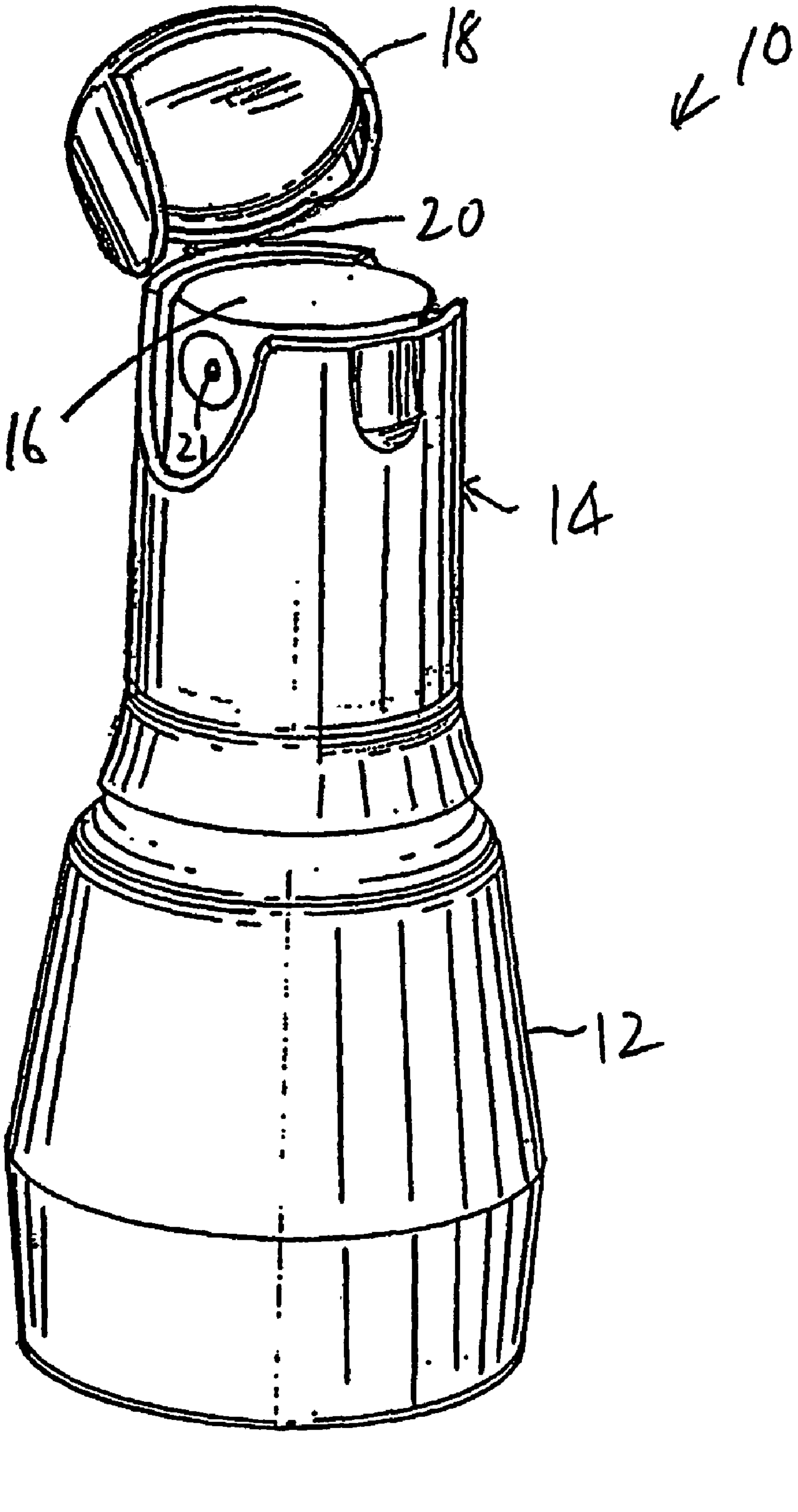

With reference to FIGS. 1 and 2, a representative pump 10 is depicted, which may include one or more of the aspects of the subject invention. The pump 10 is formed for dispensing fluid, preferably ophthalmic medication. As will be recognized by those skilled in the art, the pump 10 may be formed with any configuration; for illustrative purposes, the pump 10 includes a pump body which may include a handle 12 (which may house a fluid reservoir), a neck portion 14, a dispensing cap 16 disposed within the neck portion 14, and a flip cap 18 hingedly mounted to the neck portion 14 via a hinge 20. A nozzle 21 is formed in the dispensing cap 16 to dispense the fluid upon actuation of the pump; the actuation preferably being achieved by depressing the dispensing cap 16 and causing downward travel thereof. The pump 10 is preferably of a lift-pump type formed in accordance with the teachings set forth in U.S. Pat. No. 5,881,956 and U.S. patent application Ser. No. 10/123,390, but may also be of other pump types, such as a pre-compression type (formed in accordance with the teachings of WIPO PCT Published Application No. WO 01/14245), submersible pump type (such as that shown in WIPO PCT Published Application No. WO 02/068317), and any other form known to those skilled in the art. The inventive features described below are usable with the pump 10 and, as will be recognized by those skilled in the art, in varying combinations or singularly. The disclosures of U.S. patent application Ser. No. 10/123,390 and WIPO PCT Published Application No. WO 02/068317 are incorporated herein by reference.

Latch Fingers

As discussed in PCT Published Application No. WO 01/14245, and U.S. Pat. No. 5,881,956, the generation of sufficient momentum in actuating a microdispensing pump will avoid partial dosing, as well as, ensure sufficient momentum for a dose is provided to be properly ejected from a pump (and, therefore, properly administered).

Figure 3:
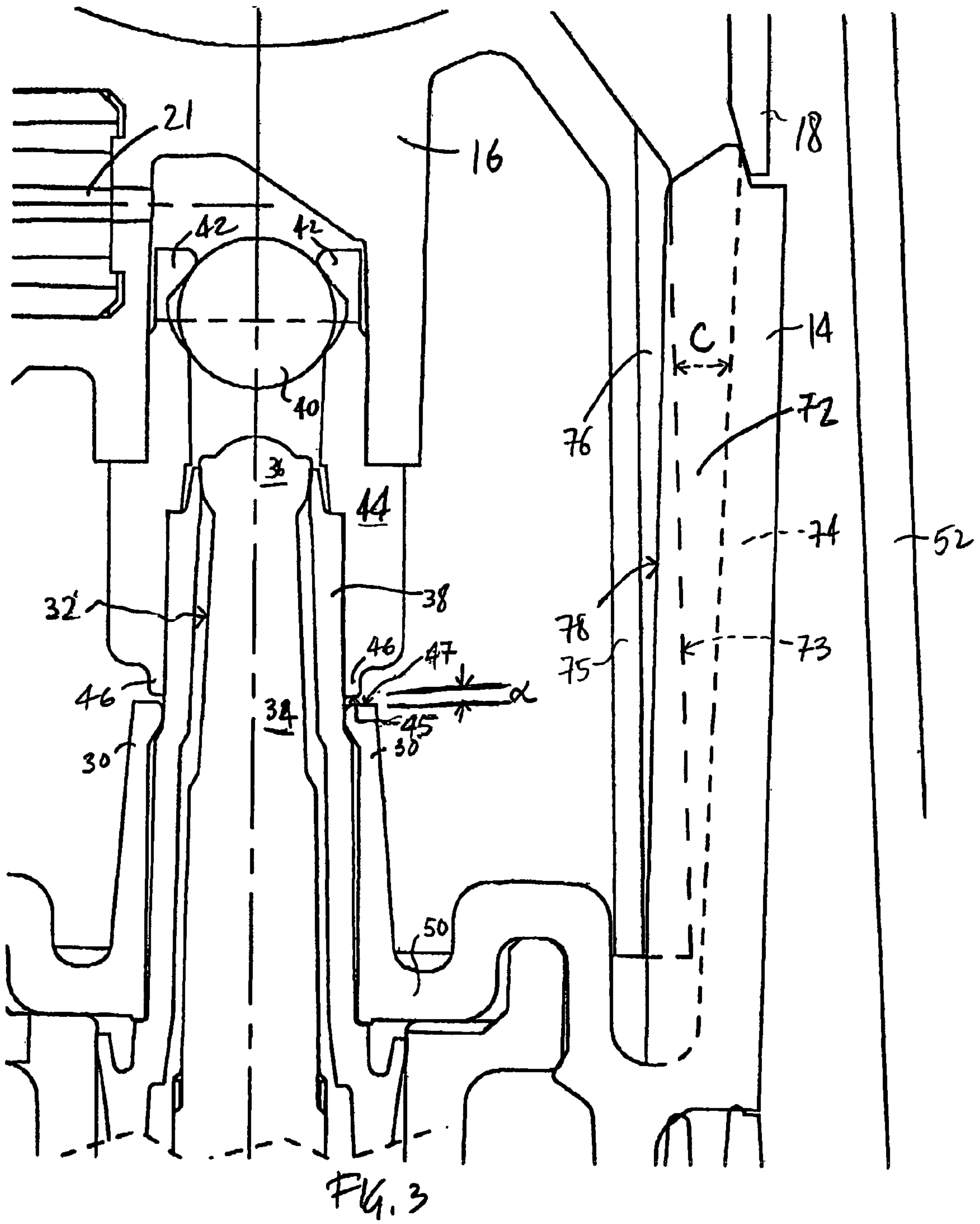
FIG. 3 is a partial cross-sectional view showing the latch fingers and ribs of the subject invention.
Figure 4:
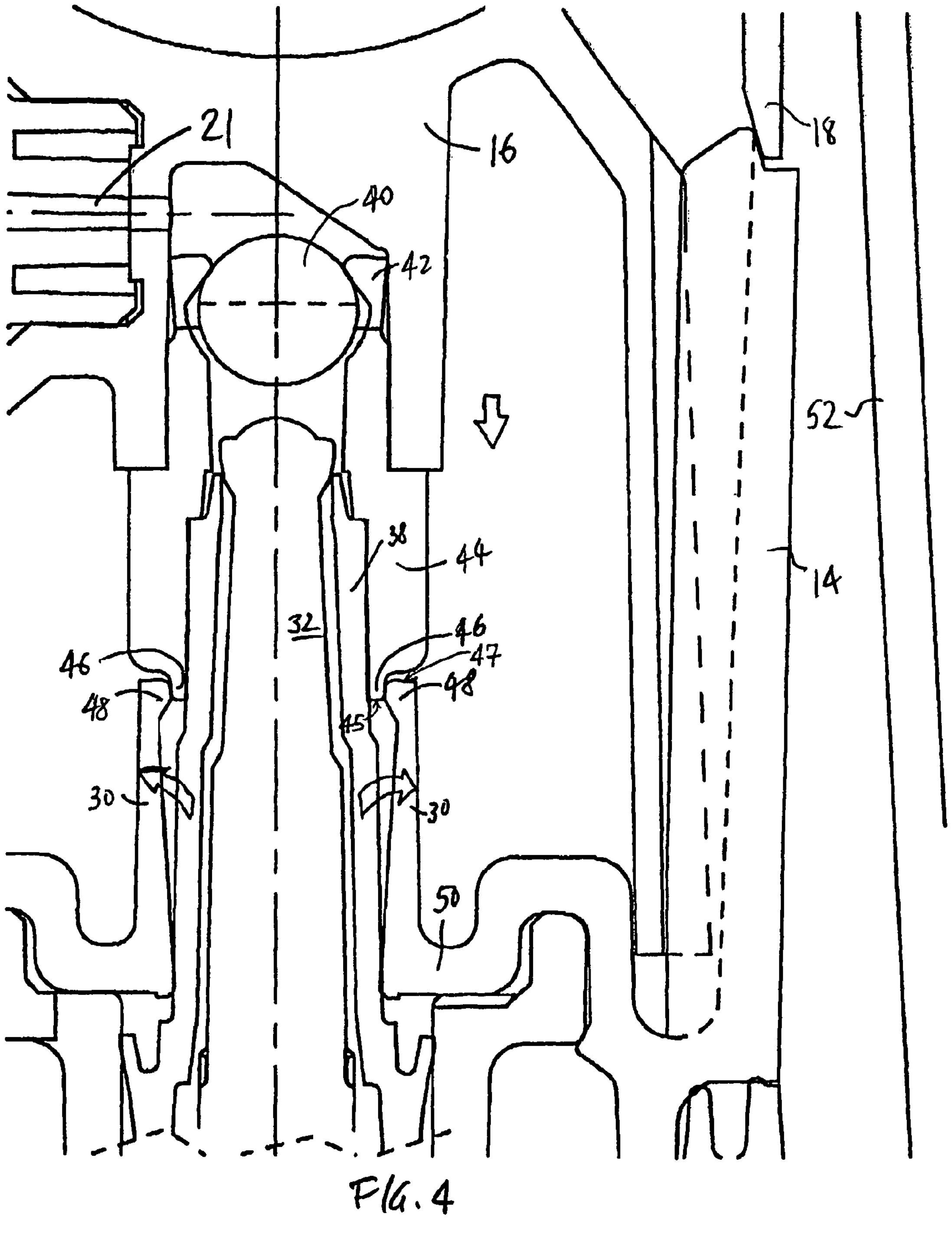
FIG. 4 is a similar view to FIG. 3, with the dispensing cap being in a depressed condition.

With reference to FIGS. 3 and 4, flexible latch fingers 30 are provided which are circumferentially disposed about a poppet 32, having a stem 34 and a head 36, and a slidable, tubular piston 38. A check valve element 40 is disposed to control the fluid dosing from the pump 10 and is controlled by spring arms 42, as described in U.S. patent application Ser. No. 10/123,390. In addition, the head 36 of the poppet 32 and the piston 38 coact to form a shut-off valve, also, as described in U.S. patent application Ser. No. 10/123,390.

A tubular element 44 extends downwardly from the spring arms 42 which terminates in an annular shoulder stop 46 that circumscribes the piston 38. As such, the shoulder stop 46 is fixed to the dispensing cap 16 so as to move in concert therewith. Alternatively, the shoulder stop 46 can be formed on any element fixed to the dispensing cap 16 or unitarily formed with the dispensing cap 16.

To actuate the pump 10, downward force is applied to the dispensing cap 16, resulting in downward movement of the shoulder stop 46, as well as the piston 38. With such downward movement, the shoulder stop 46 eventually comes into bearing engagement with the latch fingers 30, applying increasing downward force thereto commensurate with further movement of the shoulder stop 46. The latch fingers 30 restrict the ability of the tubular element 44, and thus, the piston 38, from moving downward. Upon a sufficient force being applied, as shown in FIG. 4, the latch fingers 30 deflect outwardly with the shoulder stop 46 being located between enlarged ends 48 of the latch fingers 30 and the shoulder stop 46. Thus, the piston 38 may travel its full extent and cause actuation of the pump 10—this actuation being achieved with sufficient momentum to ensure a proper dose of fluid is delivered. The movement of the piston 38 causes a dose to be administered through the nozzle 21. The piston 38 may be used to generate pressure in fluid in the pump 10 in any manner known to those skilled in the art to cause dose administration and may be formed with any known configuration (i.e., not necessarily tubular as shown in the Figures). The latch fingers 30 will not yield until a sufficient force is applied to cause the latch fingers 30 to bend radially outwardly away from the piston 38. Preferably, the latch fingers 30 are cantilevered to a unitary component 50 of the pump body of the pump 10.

As will be appreciated by those skilled in the art, the dispensing cap 16 is an actuator of the pump 10. The subject invention can be used in other pump configurations to restrict movement of an actuator, where, for example, an actuator that is separate from its dispensing aperture (e.g., an actuator which is separate from a nozzle).

Preferably, the shoulder stop 46 is annular, but may also be discontinuous. It is also preferred that the latch fingers 30 be evenly spaced about the piston 38. The shoulder stop 46 can be formed with discontinuous limited surfaces for limited engagement with one or more of the latch fingers 30.

The amount of resistance to downward movement of the shoulder stop 46 (and, thus, to downward movement of the dispensing cap 16) generated by the latch fingers 30 is a function of several factors, including, but not limited to: the constituent material of the latch fingers 30; the physical configuration of the latch fingers 30 (shape; inherent columnar stiffness; strength of cantilevered connection); and interaction between the enlarged ends 48 and the shoulder stop 46 (angle of contact; shapes; degree of friction). If insufficient resistance is provided by the latch fingers 30, the latch fingers 30 will not ensure sufficient momentum is imparted to the pump 10 upon actuation. If, however, excessive resistance is provided, the latch fingers 30 may buckle or be damaged (e.g., enlarged ends 48 could be scratched), resulting in inconsistent and unpredictable operation. It is preferred that the angle of contact between an end surface 45 of the shoulder stop 46 and top surfaces 47 of the latch fingers 30 (as represented by angle $\alpha$ in FIG. 3) be 10 degrees or less, more preferably 0 degrees. To obtain the angle $\alpha$, the end surface 45 and/or the top surfaces 47 may be tapered. It is also preferred that the surface finishes of the end surface 45 and the top surfaces 47 be dissimilar. It is further preferred that the latch fingers 30 and the shoulder stop 46 be formed from dissimilar materials. For example, the shoulder stop 46 (which may be unitarily formed with the tubular element 44) may be formed from polyethylene, whereas, the latch fingers 30 (which may be formed unitarily with the component 50) may be formed from polypropylene, or vice versa.

It is also preferred that the latch fingers 30 be formed, for example, by injection molding, into a shape which does not correspond to its undeflected state, as shown in FIG. 3. Rather, upon formation, the latch fingers 30 are bent or forced into the desired, undeflected state with the constituent material of the latch fingers 30 not having been fully solidified (e.g., upon being removed from a mold). In this manner, the latch fingers 30 are biaxially stressed with the microscopic structure thereof being aligned to impart memory to the latch fingers 30 themselves. This memory both encourages the latch fingers 30 to return more consistently to their undeflected position and to better resist stresses and strains of repeated operation. This same manufacturing technique is preferably used with the spring arms 42. It is preferred that, in undeflected states, the latch fingers 30 bear against the outer surface of the piston 38, and the spring arms 42 bear against the check valve element 40.

Overcap

Figure 5:
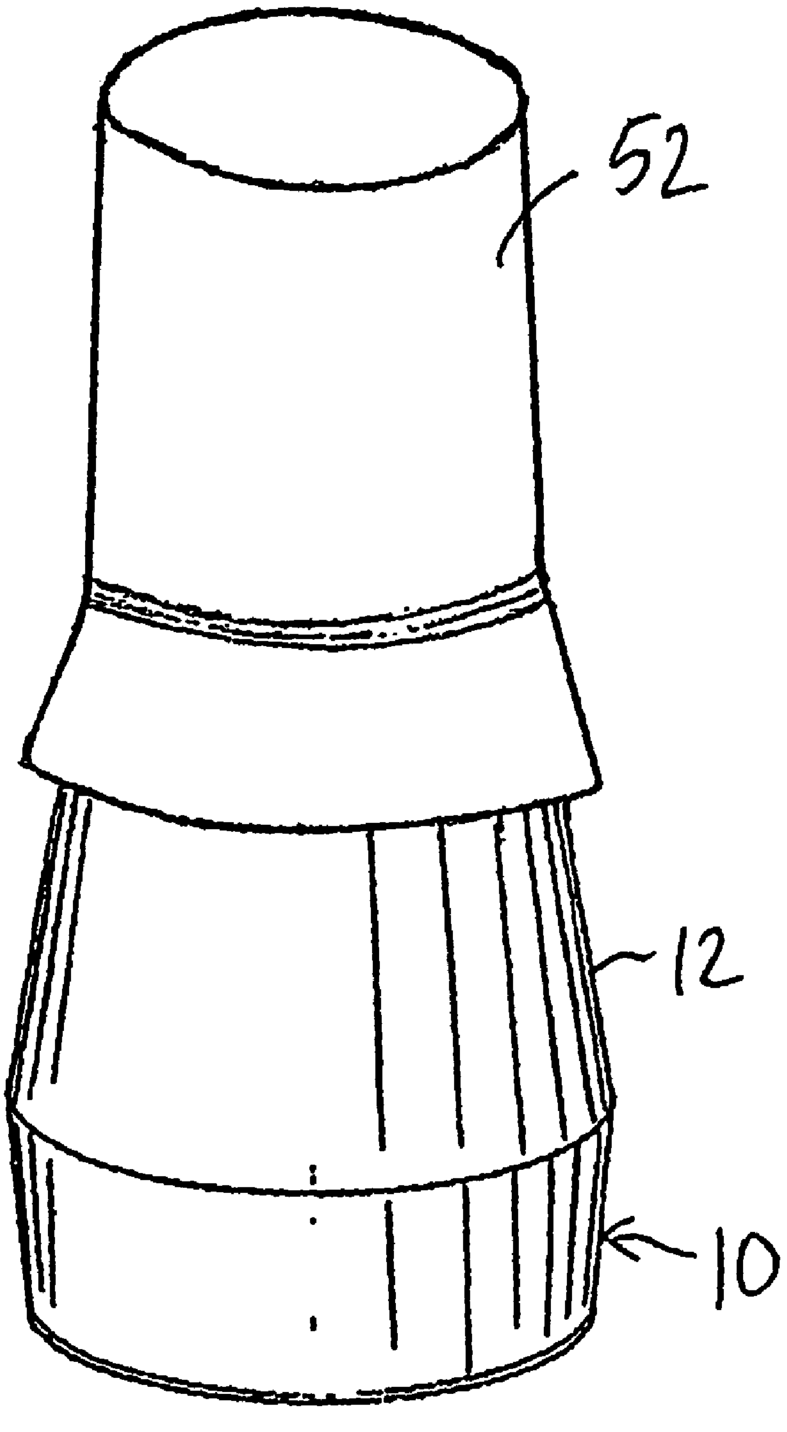
FIG. 5 is a perspective view of a pump having an overcap mounted thereto.

With reference to FIG. 5, an overcap 52 may be provided which mounts onto, and forms a seal with, the handle 12 of the pump body. Advantageously, the overcap 52 completely encompasses and protects the dispensing cap 16, and all components thereabout, including the nozzle 21. With a seal being formed at locations spaced from the dispensing cap 16 and the nozzle 21, the ingress of dirt and debris thereinto may be minimized. It is preferred that the overcap 52 form at least a liquid-tight, and, preferably, a fluid-tight seal with the pump body.

Figure 6:
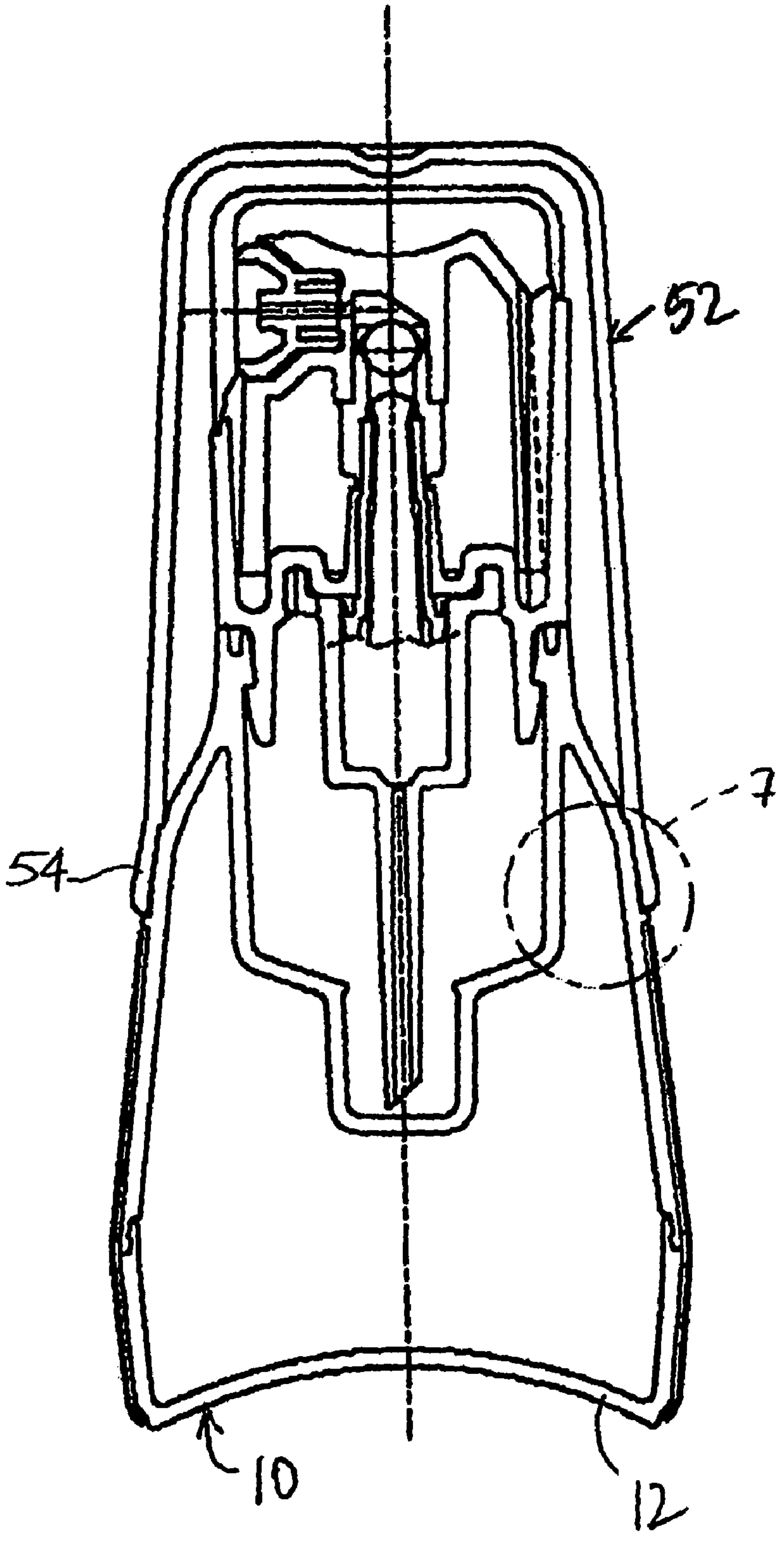
FIG. 6 is a cross-sectional view of FIG. 5.

With reference to FIG. 6, the overcap 52 is preferably unitarily formed and has a cup shape. Edge 54 of the overcap 52 is placed into engagement with the handle 12 upon the overcap 52 being mounted to the pump body of the pump 10.

Figure 7:
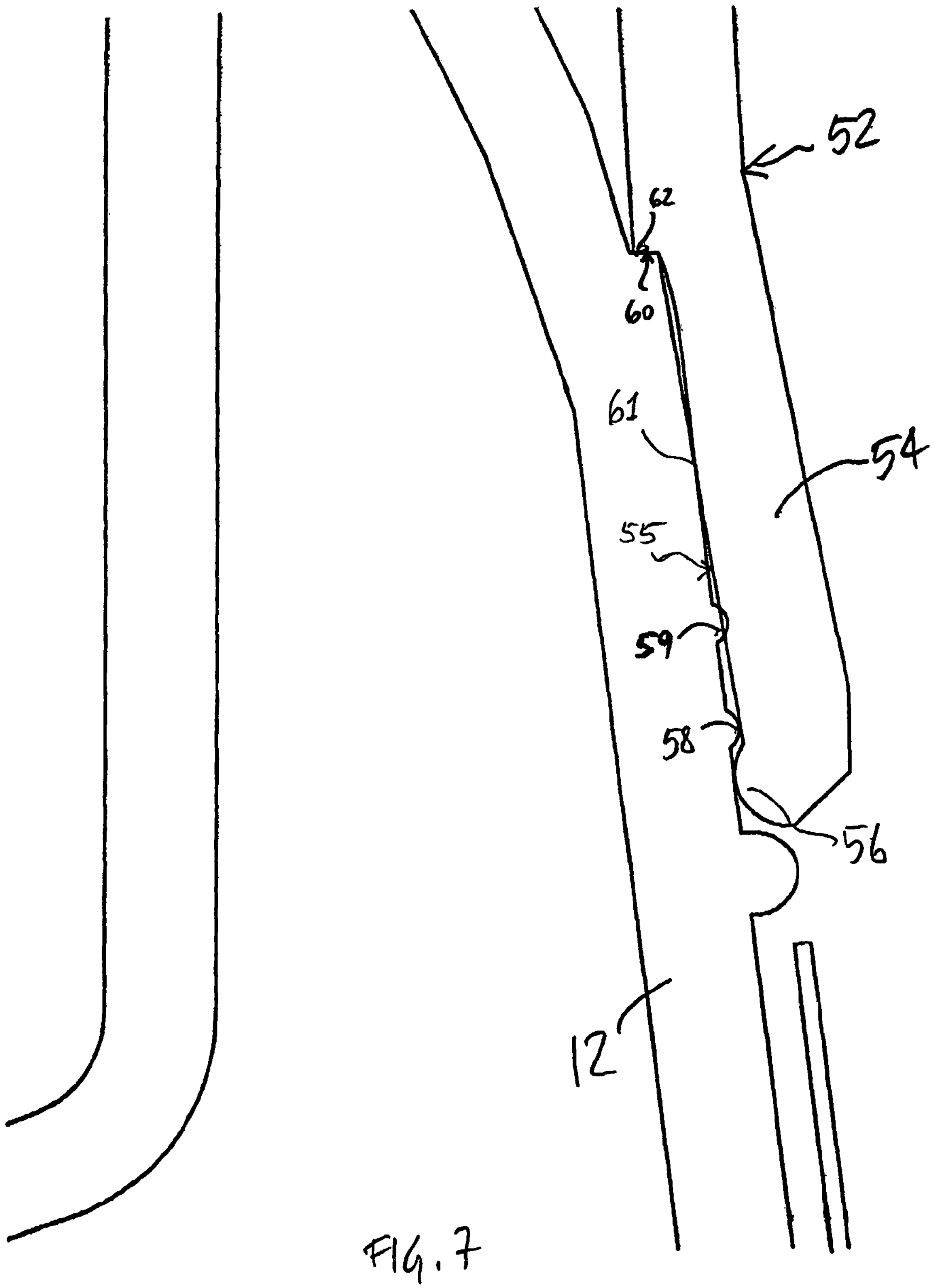
FIG. 7 is an enlarged sectional view of section 7 of FIG. 6.

With reference to FIG. 7, the edge 54 is preferably formed to flare outwardly and to terminate in at least one retention bead 56. The shape of the edge 54 preferably matches that of the handle 12 of the pump body. At least two beads 58, 59 protrude from an external surface of the handle 12 of the pump body which are positioned to engage the overcap 52 above the large bead 56. The lower bead 58 is a retention bead formed to interferently engage the retention bead 56 upon upward movement of the overcap 52 to inhibit removal of the overcap 52. In a mounted position of the overcap 52, the retention bead 56 extends inwardly of the lower bead 58.

The upper bead 59 is formed to interferently engage an inner surface 55 of the overcap 52 to define a fluid-tight/liquid-tight seal. (The outline of the upper bead 59 is shown to overlap the edge 54 to represent this interferent engagement.) In addition, the overcap 52 may be formed to be stressed in a mounted position to enhance the seal's integrity such as by defining one or more contact points 61 between the inner surface 55 and the handle 12. The upper bead 59 and the contact points 61 define redundant seals in giving the pump 10/overcap 52 assembly the liquid-tight/fluid-tight seal. The strength of the seal may be adjusted for the pump's application; for example, where some gas permeability may be desired, a fluid-tight seal is not appropriate.

The contact points 61 can be defined as a self-holding taper fit (e.g., a Morse-taper type fit) which not only defines an at least liquid-tight seal, but also provides holding force for the overcap 52 to the pump body. With sufficient holding force and/or sealing integrity, the retention bead 56, the lower bead 58 and/or the upper bead 59 need not be provided. It is preferred that the inner surface 55 and the handle 12 define a taper angle in the range of 0°–7°, more preferably 1°–2.5°, at the contact points 61 to define the self-holding taper fit.

It is preferred that the constituent material, preferably plastic, of the overcap 52 be resilient to allow the edge 54 to expand outwardly upon mounting the overcap 52 so that the retention bead 56 may pass over the beads 58, 59. The material, however, must have sufficient memory to ensure sufficiently tight engagement of the bead 59 with the overcap 52. It is further preferred that cooperating shoulders 60 and 62 be formed on the overcap 52 and the handle 12 of the pump body, respectively, to limit the downward movement of the overcap 52, thereby allowing for proper positioning thereof.

Beads For Protecting Label

Figure 8:
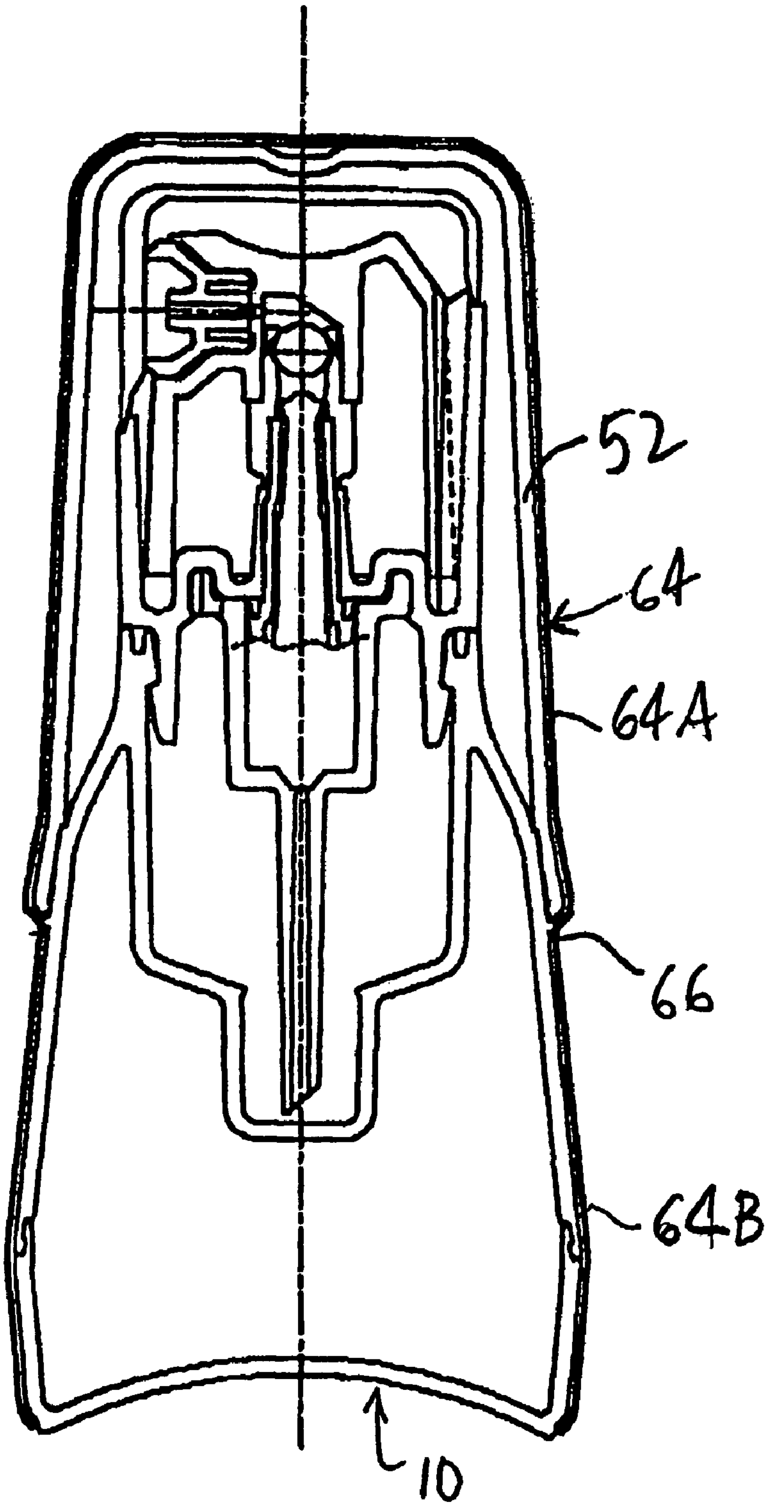
FIG. 8 is a schematic showing a label disposed about the pump.

Referring to FIG. 8, the pump 10 may be packaged with a clear or printed-on label 64. Typically, the printed-on label 64 is shrunk onto ("shrink wrapped" onto) the pump 10. As shown in FIG. 8, the label 64 preferably extends the full length of the pump 10/overcap 52 assembly to provide an additional holding force for maintaining the overcap 52 on the pump 10 and to indicate any tampering with the pump 10 prior to initial use. For removal, a weakened portion 66, such as a tear line defined by an array of perforations, is defined just below the overcap 52, so that upon forcibly removing the overcap 52, the label 64 is severed into an upper portion *64a* and a lower portion *64b*.

Figure 9:
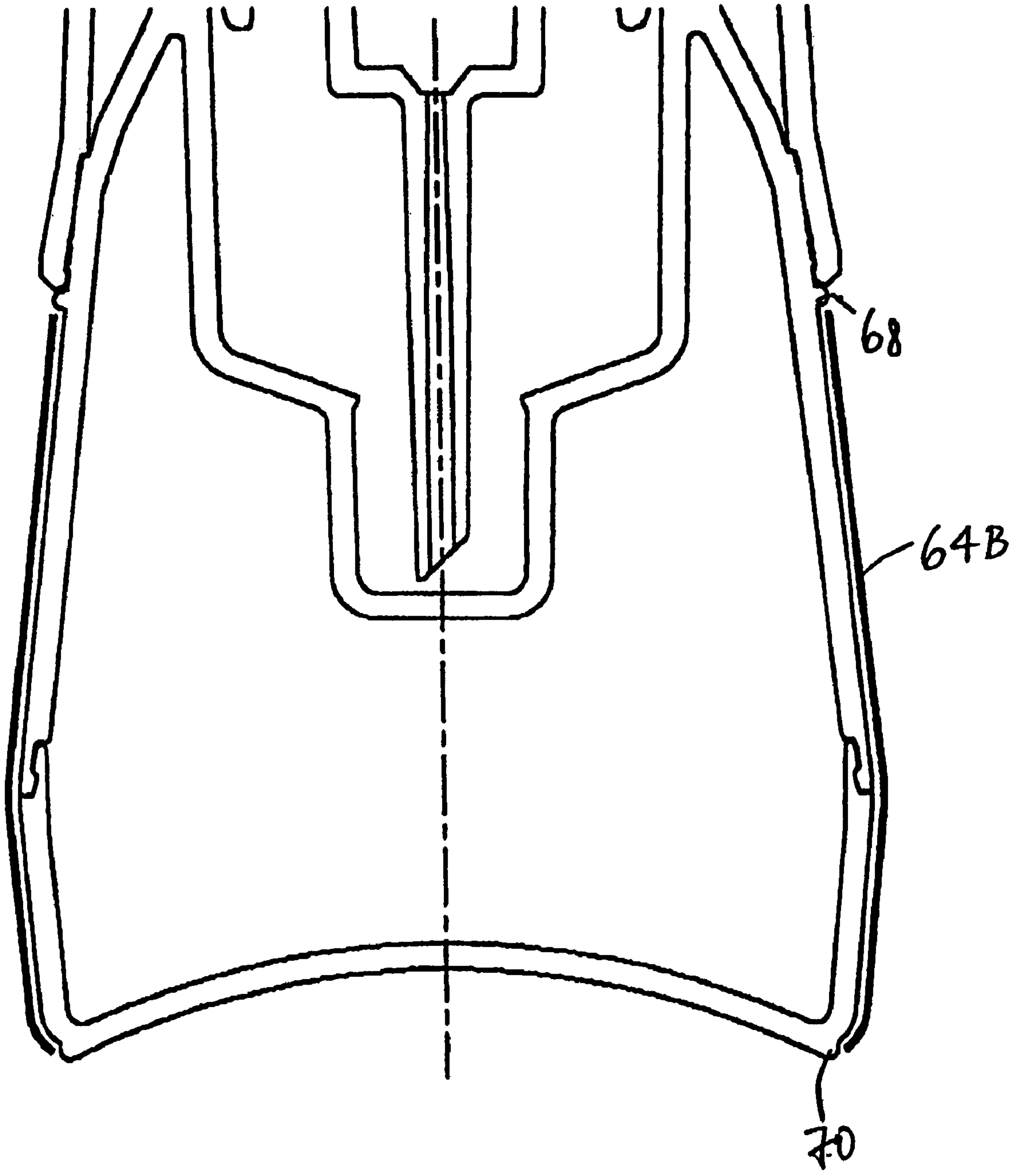
FIG. 9 is a partial cross-sectional view showing a lower portion of the label and protective beads disposed in proximity thereto.

It may be desirable to maintain the lower portion *64b* of the label 64 on the pump 10, for aesthetic and/or marketing purposes. Additionally, the lower portion *64b* may contain instructions and other vital information, such as warnings, relating to the fluid that is to be dispensed by the pump 10. Accordingly, to restrict the ability of a user in removing the lower portion *64b* of the label 64, protective beads 68 and 70 (FIG. 9) are disposed in proximity to the upper and lower edges of the lower portion *64b*. The protective beads 68 and 70 limit a person's ability to pry or otherwise insert an object or a fingernail under the lower portion *64b* and cause removal thereof. Preferably, the protective beads 68 and 70 extend continuously about the pump 10 and are coextensive with the lower portion *64b*. It is preferred that the upper protective bead 68 be positioned adjacent to the weakened region 66 of the label 64 (when intact), and also in proximity to the edge 54 of the overcap 52 (FIG. 9).

As is readily apparent, optionally, one of the protective beads 68, 70 may be provided. Also, the label 64 can be wholly formed to be disposed in proximity to one or both of the protective beads 68, 70 (e.g., formed only as the lower portion *64b*). Also, the label 64, including any part thereof, can be affixed to the pump 10 in any manner known to those skilled in the art, including being adhered thereto.

Reduction of Dispensing Cap Float

With reference to FIGS. 3 and 4, the dispensing cap 16 is mounted to move with the piston 38 to actuate the pump 10, such as via the tubular element 44. Because of the slender construction of the piston 38 and the tubular element 44, and because these elements are movable, the dispensing cap 16 may have some lateral instability. Furthermore, because of manufacturing tolerances, a clearance C is between the dispensing cap 16 and the neck portion 14. Accordingly, the dispensing cap 16 may move laterally during actuation, for example under eccentric loading, and float into the clearance C. With the dispensing cap 16 "floating" into the clearance C, downward force may be applied obliquely to the tubular element 44 and/or to the piston 38, resulting in uneven loading on the latch fingers 30, on various seal faces, and/or other components of the pump 10.

To minimize float, at least one rib 72 extends from a side wall 74 (preferably, the side wall 74 is a portion of the neck portion 14) of the pump body of the pump 10 so as to engage or come into close proximity with the dispensing cap 16. Preferably, a plurality of circumferentially spaced ribs 72 are utilized. With the dispensing cap 16 being tapered (tapered skirt 75), as shown in FIGS. 3 and 4, lower portions of the ribs 72 are in closer engagement with the dispensing cap 16 than upper portions. With the ribs 72, float of the dispensing cap 16 can be greatly minimized or even altogether eliminated, resulting in generally straight downward movement of the dispensing cap 16 during actuation. The ribs 72 may engage an outer surface 73 of the dispensing cap 16 or, more preferably, extend into corresponding channels 76 formed in the dispensing cap 16. It is preferred that the ribs 72 have generally straight outer faces 78 (0 degrees of draft) and that a clearance of 0.001 to 0.005 inches be defined between the ribs 72 and the associated opposing surface (the outer surface 73/the channels 76).

With reference to FIGS. 3 and 4, the dispensing cap 16 has a range of movement in actuating the pump 10 (FIG. 3 is an at-rest position of the dispensing cap 16; FIG. 4 is a depressed position of the cap 16). The ribs 72 are formed with sufficient length to at least extend substantially along the dispensing cap 16 for full extent of movement of the dispensing cap 16; where the channels 76 are provided, the ribs 72 are formed with sufficient length to at least extend substantially through the length of the respective channel 76 along full extent of movement of the dispensing cap 16. Preferably, the ribs 72 are substantially coextensive with the respective channels 76. As such, the ribs 72 act to limit lateral movement of the dispensing cap 16 throughout its range of movement.

As with previous aspects of the subject invention, this aspect can be used with various pump actuators and/or pump configurations. As a further variation, the ribs 72 may be formed on the dispensing cap 16, and the channels 76, if used, on the side wall 74.

Various changes and modifications can be made to the present invention. It is intended that all such changes and modifications come within the scope of the invention as set forth in the following claims.

What is claimed is:

1. A pump for dispensing fluid, said pump comprising:

a pump body;

a plurality of cantilevered fingers disposed within said pump body;

a piston disposed to slidably move at least partially within said fingers; and, a stop member at least partially disposed about said piston, wherein said stop member and said fingers being fixed to said pump body such that movement of said piston results in relative movement between said fingers and said stop member, wherein said stop member is located to be contacted by said fingers upon a predetermined extent of relative movement between said stop member and said fingers, said fingers flexing upon contacting said stop member such that said fingers yieldingly inhibit movement of said piston, whereby a predetermined amount of force is required to overcome the inhibition of movement of said piston so as to enable operation of the pump.

2. A pump as in claim 1, wherein said fingers are evenly spaced about said piston.

3. A pump as in claim 1, wherein said stop member is annular.

4. A pump as in claim 1, wherein said stop member terminates in an end surface for contacting said fingers, said end surface being tapered.

5. A pump as in claim 4, wherein said fingers each having a top surface for contacting said stop member, said top surface being tapered.

6. A pump as in claim 1, wherein said fingers each having a top surface for contacting said stop member, said top surface being tapered.

7. A pump as in claim 1, wherein said stop member and said fingers are formed from different materials.

8. A pump as in claim 1, wherein said stop member terminates in an end surface for contacting said fingers, said fingers each having a top surface for contacting said stop member, said end surface and said top surfaces having different surface finishes.

9. A pump for dispensing fluid, said pump comprising:

a pump body including a movable dispensing cap with a nozzle, said dispensing cap being movable to actuate the pump, and at least one rib extending into close proximity to an outer surface of said dispensing cap, each said rib having a sufficient length to at least extend substantially along said dispensing cap for full extent of movement of said dispensing cap.

10. A pump for dispensing fluid, said pump comprising:

a pump body;

a plurality of cantilevered fingers disposed within said pump body;

a movable actuator for causing dispensing of the pump; and, a stop member fixed to said actuator, wherein movement of said actuator results in movement of said stop member, wherein said stop member is located to be contacted by said fingers upon a predetermined extent of relative movement between said stop member and said fingers, said fingers flexing upon contacting said stop member such that said fingers yieldingly inhibit movement of said actuator, whereby a predetermined amount of force is required to overcome the inhibition of movement of said actuator so as to enable operation of the pump.

11. A pump as in claim 10, wherein said actuator is a dispensing cap having a nozzle formed therein for dispensing fluid.

12. A pump as in claim 10, wherein said stop member is annular.

13. A pump as in claim 10, wherein said stop member terminates in an end surface for contacting said fingers, said end surface being tapered.

14. A pump as in claim 13, wherein said fingers each having a top surface for contacting said stop member, said top surface being tapered.

15. A pump as in claim 10, wherein said fingers each having a top surface for contacting said stop member, said top surface being tapered.

16. A pump as in claim 10, wherein said stop member and said fingers are formed from different materials.

17. A pump as in claim 10, wherein said stop member terminates in an end surface for contacting said fingers, said fingers each having a top surface for contacting said stop member, said end surface and said top surfaces having different surface finishes.

* * * * *